US00PP34957P2

(12) United States Plant Patent
Nizinski

(10) Patent No.: US PP34,957 P2
(45) Date of Patent: Jan. 31, 2023

(54) ***ILEX* PLANT NAMED 'DRO-IMT'**

(50) Latin Name: *Ilex crenata*
Varietal Denomination: 'DRO-IMT'

(71) Applicant: Plants Nouveau, LLC, Mobile, AL (US)

(72) Inventor: David Nizinski, Dutton, VA (US)

(73) Assignee: Plants Nouveau, Mobile, AL (US)

( * ) Notice: Subject to any disclaimer, the term of this patent is extended or adjusted under 35 U.S.C. 154(b) by 0 days.

(21) Appl. No.: 17/950,160

(22) Filed: Sep. 22, 2022

(51) Int. Cl.
*A01H 5/12* (2018.01)
*A01H 6/00* (2018.01)

(52) U.S. Cl.
USPC ..... Plt./247

(58) Field of Classification Search
USPC ..... Plt./247
CPC ..... A01H 5/12; A01H 5/00; A01H 6/00
See application file for complete search history.

*Primary Examiner* — June Hwu
(74) *Attorney, Agent, or Firm* — Cassandra Bright

(57) ABSTRACT

A new and distinct *Ilex* cultivar named 'DRO-IMT' is disclosed, characterized by distinctive yellow-green. Foliage is elliptic in shape. Plants have a columnar habit. Plants are very well suited for performance in the landscape, including as a specimen plant or mass planting. The new cultivar is an *Ilex*, suitable for ornamental garden purposes.

2 Drawing Sheets

Latin name of the genus and species: *Ilex crenata.*
Variety denomination: 'DRO-IMT'.

BACKGROUND OF THE INVENTION

The new cultivar is a product of chance discovery by the inventor, in his home garden in Dutton, Va. during April of 2015. This new variety, hereinafter referred to as 'DRO-IMT', was discovered as a naturally occurring, single branch mutation of the parent variety *Ilex crenata*, 'Sky Pencil', unpatented.

After identifying the new variety as a potentially interesting selection, the inventor first organized propagation of 'DRO-IMT' by softwood vegetative cuttings during July of 2015 at a private commercial nursery in Saluda, Va. The inventor continued controlled testing and propagation, assessing stability of the unique characteristics of this variety. Numerous generations have been reproduced and have shown that the unique features of this cultivar are stable and reproduced true to type.

SUMMARY OF THE INVENTION

The cultivar 'DRO-IMT' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DRO-IMT' These characteristics in combination distinguish 'DRO-IMT' as a new and distinct *Ilex* cultivar:

1. Stable and distinctive Yellow-Green foliage.
2. Distinctive elliptical foliage.
3. Columnar plant growth.

COMPARISON TO PARENT VARIETY

The new variety differs from the parent variety in having a less vigorous plant habit. Additionally, the new variety has distinctive Yellow-Green foliage not seen in the parent variety, which has dark green foliage.

COMMERCIAL COMPARISON

'DRO-IMT' can be compared to the commercial variety *Ilex vomitoria* 'Will Fleming', unpatented. Plants of the new cultivar 'DRO-IMT' are similar to plants of 'Will Fleming' in some horticultural characteristics, however, plants of the new cultivar 'DRO-IMT' differ in the following:

1. 'DRO-IMT' has a much denser plant habit
2. Foliage of the new variety is distinctively yellow-green; foliage of this comparator is dark green.

'DRO-IMT' can be compared to the commercial variety *Ilex crenata* 'Mariesii', unpatented. Plants of the new cultivar 'DRO-IMT' are similar to plants of 'Mariesii' in most horticultural characteristics, however, plants of the new cultivar 'DRO-IMT' differ in the following;

1. 'DRO-IMT' has a more narrow plant habit
2. Foliage of the new variety is distinctively yellow-green, foliage of this comparator is yellow-green when first emerging, turning dark green with maturity.
3. Foliage of the new variety is distinctively elliptical in shape; foliage of this comparator is broad ovate.
4. Stems of the new variety are green; stems of this comparator are greyed-red.

BRIEF DESCRIPTION OF THE PHOTOGRAPHS

Figure 1:
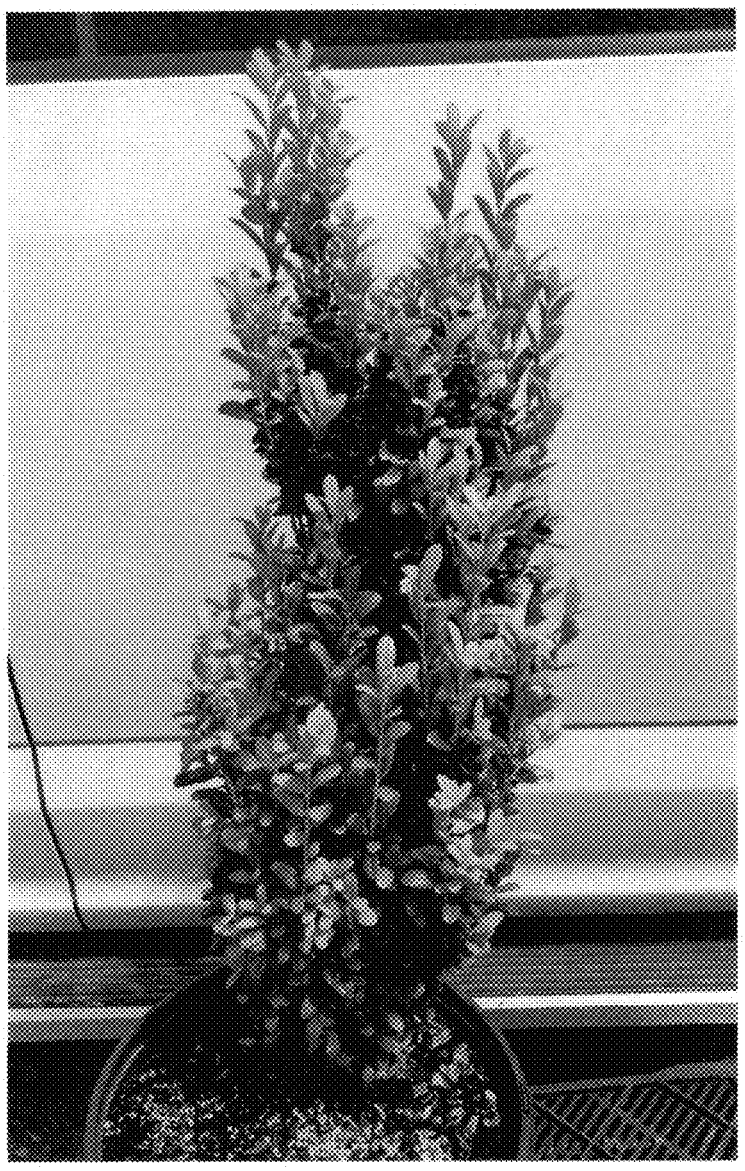

The accompanying photograph in FIG. 1 illustrates in full color a 2 year old plant of the new variety in a 3 gallon pot.

Figure 2:
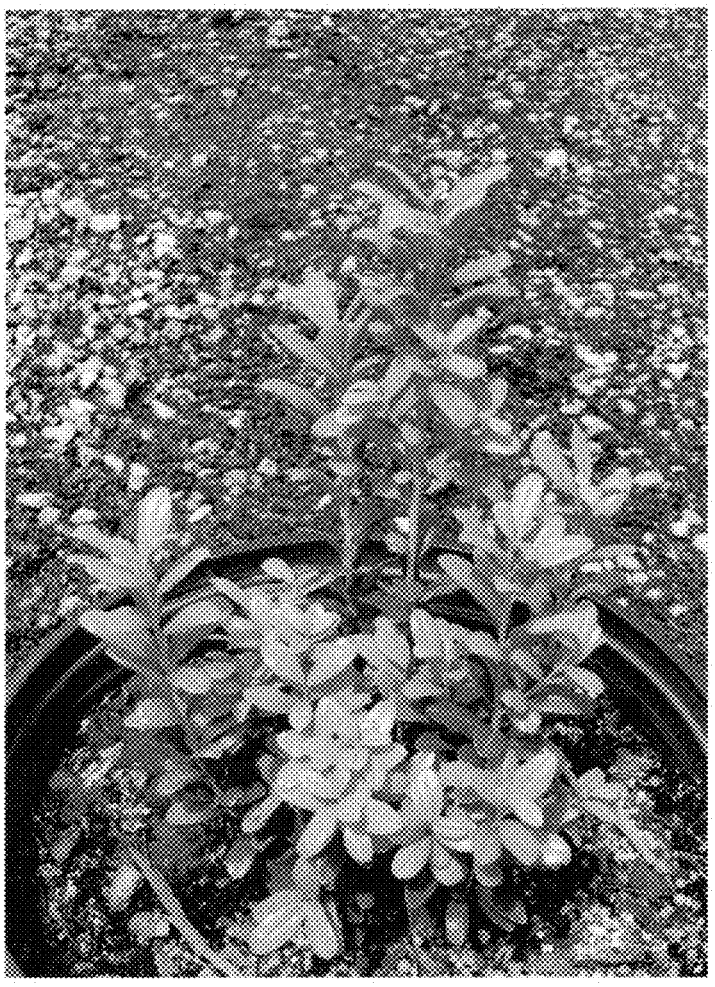

FIG. 2 illustrates a close-up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'DRO-IMT' plants grown outdoors in Loxley, Ala. Plants are approximately 1.5 years old, in a 3-gallon nursery container. Measurements and numerical values represent averages of typical plant types.

Botanical classification: *Ilex crenata* 'DRO-IMT'.

PROPAGATION

Typically by softwood cuttings in Spring and Summer.

Root description: Very dense fibrous roots. Colored near RHS Grey-Brown 199C. Somewhat shallow rooted.

PLANT

Growth habit: Upright evergreen shrub. Columnar.

Height: Approximately 42 cm.

Plant spread: Approximately 20 cm.

Branching characteristics: Densely branched, approximately 6 to 8 primary branches are densely clustered near the base of the plant (about 3 cm to 5 cm from soil level). A pinch given at approximately 10 cm from the soil level results in 7 to 9 densely occurring stems. Stems/Branches occur at 10° to 15° angles.

Primary branches:

Length of primary branches: Average range 15 to 20 cm, then branching into further acute lateral stems.

Diameter of primary branches: Approximately 5 mm.

Primary branch strength: Very strong, difficult to break.

Primary branch color: Oldest wood near RHS Yellow-Green 144B with thin covering of Grey-Brown 199B. Immature branches near Yellow-Green 144B.

Primary branch texture: Glabrous. Oldest wood somewhat rough.

Lateral branches:

Length of lateral branches: Average range 9 to 15 cm.

Diameter of lateral branches: Average 3 mm.

Lateral branch strength: Strong.

Lateral branch color: Near RHS Yellow-Green 144C.

Lateral branch texture: Glabrous, smooth.

FOLIAGE

Leaf:

*Type*.—Simple.

*Arrangement*.—Spiraling around stem.

*Average length*.—2.5 cm.

*Average width*.—*Approximately* 1 cm.

*Shape of blade*.—Elliptical.

*Apex*.—Broadly tapering to rounded.

*Base*.—Broadly tapering.

*Leaf internode length*.—About 5 mm.

*Attachment*.—Stalked.

*Margin*.—Entire.

*Texture of top surface*.—Glabrous.

*Texture of bottom surface*.—Glabrous.

*Appearance of top surface*.—Glossy.

*Appearance of bottom surface*.—Matte.

*Color*.—Young foliage upper side: Near RHS Yellow-Green 151B with overall hue near 154A. Young foliage under side: Near RHS Yellow-Green 154C. Mature foliage upper side: Near RHS Yellow-Green N144C. Mature foliage under side: Near RHS Yellow-Green N144D.

Venation:

*Type*.—Pinnate.

*Venation color upper side*.—Near RHS Yellow-Green 154C.

*Venation color under side*.—Near RHS Yellow-Green 145B.

Petiole:

*Length*.—About 2 to 5 mm.

*Diameter*.—About 2 mm.

*Color*.—Upper Surface: Near RHS Yellow-Green N144A. Lower Surface: Near RHS Yellow-Green N144A.

FLOWER

Not observed to date.

OTHER CHARACTERISTICS

Disease and pest resistance: Neither resistance nor susceptibility to normal diseases and pests of *Ilex* observed. Potential insect problems include holly leaf miner, spider mites, whitefly and scale. Potential disease problems include leaf spot, leaf rot, tar spot and powdery mildew.

Temperature tolerance: USDA Zone 5 through 9.

Fruit/seed production: Not observed to date.

What is claimed is:

1. A new and distinct cultivar of *Ilex* plant named 'DRO-IMT' as herein illustrated and described.

* * * * *